United States Patent
Salter et al.

(10) Patent No.: US 11,427,849 B2
(45) Date of Patent: Aug. 30, 2022

(54) CULTURE MEDIUM METHOD AND DEVICE

(71) Applicant: Charm Sciences, Inc., Lawrence, MA (US)

(72) Inventors: Robert S. Salter, Reading, MA (US); Gregory W. Durbin, Northborough, MA (US); Stanley E. Charm, Boston, MA (US); Richard T. Skiffington, North Reading, MA (US)

(73) Assignee: Charm Sciences, Inc., Lawrence, MA (US)

( * ) Notice: Subject to any disclaimer, the term of this patent is extended or adjusted under 35 U.S.C. 154(b) by 1502 days.

(21) Appl. No.: 14/426,220

(22) PCT Filed: Sep. 16, 2013

(86) PCT No.: PCT/US2013/059931
§ 371 (c)(1),
(2) Date: Mar. 5, 2015

(87) PCT Pub. No.: WO2014/043616
PCT Pub. Date: Mar. 20, 2014

(65) Prior Publication Data
US 2016/0040211 A1    Feb. 11, 2016

Related U.S. Application Data

(60) Provisional application No. 61/876,413, filed on Sep. 11, 2013, provisional application No. 61/738,153, filed on Dec. 17, 2012, provisional application No. 61/718,245, filed on Oct. 25, 2012.

(51) Int. Cl.
*C12Q 1/04*    (2006.01)
(52) U.S. Cl.
CPC .................... *C12Q 1/045* (2013.01)
(58) Field of Classification Search
CPC ............ C12Q 1/045; C12N 1/22; C12N 1/20
See application file for complete search history.

(56) References Cited

U.S. PATENT DOCUMENTS

| | | | |
|---|---|---|---|
| 6,243,486 B1 | 6/2001 | Weiss | 382/133 |
| 6,265,203 B1 | 7/2001 | Ushiyama | 435/253.6 |
| 6,381,353 B1 | 4/2002 | Weiss | 382/133 |
| 2005/0239200 A1 | 10/2005 | Beckwith et al. | 435/299.1 |
| 2010/0233146 A1* | 9/2010 | McDaniel | A01N 63/02 424/94.2 |
| 2010/0273260 A1 | 10/2010 | Odane et al. | 435/396 |
| 2011/0177148 A1* | 7/2011 | Dicosimo | A01N 25/02 424/411 |
| 2011/0250626 A1* | 10/2011 | Williams | A01N 63/02 435/18 |
| 2012/0121543 A1 | 5/2012 | Teather et al. | 424/93.2 |

FOREIGN PATENT DOCUMENTS

| | | | |
|---|---|---|---|
| WO | WO1995014452 | 6/1995 | D04H 1/56 |
| WO | WO2012/092181 | 7/2012 | C12Q 1/04 |

OTHER PUBLICATIONS

Guerini et al. "Evaluation of *Escherichia coli* O157:H7 Growth Media for Use in Test-and-Hold Procedures for Ground Beef Processing" U.S. Department of Agriculture, Agricultural Research Service, Roman L. Hruska U.S. Meat Animal Research Center, Clay Center, Nebraska 68933-0166, USA.*

* cited by examiner

*Primary Examiner* — Blaine Lankford
(74) *Attorney, Agent, or Firm* — MacCord Mason PLLC

(57) ABSTRACT

Culture medium devices and systems are shown and described. In one embodiment, the device comprises a culture medium adapted for test fluid inoculation without the concerns associated with a spreading step. In particular examples, a printed grid on the outer surface of a culture device is visible on the inner surface for colony counting after a test has been developed. The result is a device that allows for detection, identification, and transportation of various microorganisms without preparation or spreading steps, and more particularly to a culture medium in which a test fluid inoculated thereto diffuses rapidly.

17 Claims, 2 Drawing Sheets

CULTURE MEDIUM METHOD AND DEVICE

This application is based on and claims priority to U.S. Provisional Patent Application No. 61/701,123, filed Sep. 14, 2012; U.S. Provisional Patent Application No. 61/718, 245, filed Oct. 25, 2012; U.S. Provisional Patent Application No. 61/738,153, filed Dec. 17, 2012; and U.S. Provisional Patent Application No. 61/876,413, filed Sep. 11, 2013, the teachings of which are hereby incorporated by reference in their entireties.

FIELD OF THE TECHNOLOGY

The present disclosure relates generally to analytical testing, and more particularly to improved culture media methods and devices.

BACKGROUND

It is desirable to provide rapid, effective detection and identification of various and numerous microorganisms in test samples, such as samples of water, food, such as milk, and body fluids. Microorganisms of interest include all aerobic bacteria and specific bacterial groups, such as coliforms. Other microorganisms of interest include a variety of molds and the like.

Classical methods for culturing various microorganisms for detection and identification thereof include the spread plate method, the pour plate method and the liquid medium method. These methods, however, require preparation by technicians. Such preparation includes mixing, heating and pouring, sterilization of culture medium, apparatus, sample spreading etc. before culture of microorganisms, and inoculation of a test sample into the medium.

In methods and devices that utilize water-absorbing elements, such as sponges and/or filter paper, colony growth may not be sufficiently contained, thereby limiting the quantitative value of such devices, and making microorganism colony isolation impractical. In addition, some such structures are not sufficiently transparent to allow for the counting of colonies through the substrate.

Particularly in the food industry, testing is very cost-sensitive. In addition, users might not be laboratory-trained technicians. Tests used must, therefore, be user-friendly and inexpensive without sacrificing accuracy.

One example of a commercially available product that eliminates some or all of the above concerns is known as PETRIFILM (3M, St. Paul, Minn.).

Applicants desire an alternative user-friendly culture medium, device and method that is useful, for example, for detection, identification, and transportation of various microorganisms, and more particularly to a culture medium in which a test fluid inoculated thereto diffuses rapidly.

SUMMARY

In accordance with the present disclosure, a culture medium is provided for detection, identification, transportation of various microorganisms. This disclosure provides an improved medium and system that is convenient, efficient, and safe for the user.

One aspect of the present disclosure is to provide a culture medium mixture to be applied to a device having a flat surface. The culture medium mixture may include an adhesive; a gelling agent; a bacterial nutritive ingredient; a fibrous material; a percent liquid organic solvent; and a cellulosic material. Typically, wherein upon drying or evaporation of the mixture on the device, the mixture forms a liquid absorbent matrix. The matrix may have a uniform distribution of bacterial growth media that is adapted to absorb and evenly diffuse a liquid sample throughout the absorbent matrix.

In some examples, the gelling agent may be xanthan gum, tica gum, locust bean gum, guar gum, carrageenan, alginate, the like and a combination thereof. The adhesive agent may be hydroxypropylcellulose, hydroxylmethylcellulose, solvent soluble cellulosics, the like and a combination thereof. The bacterial nutritive ingredient may comprise EC media. The bacterial nutritive ingredient may comprise plate count agar, plate count agar individual components, the like and a combination thereof. The bacterial nutritive ingredient may comprise yeast and mold growth media. For instance, the bacterial nutritive ingredient may comprise potato dextrose broth.

In particular examples, the bacterial nutritive ingredient may comprise selective medium for growth of indicator organisms. For instance the bacterial nutritive ingredient may comprise growth promoters for bacteria such as coliform, *E. coli, enterobacteriaceae,* or pathogens. The bacterial nutritive ingredient may comprise growth promoters for pathogens, such as *salmonella, listeria,* or *camphlobacter*.

In some examples, the organic solvent comprises ethanol, isopropyl alcohol, the like and a combination thereof. The alcohol percentage may be more than about 50%, including about 60-80%. The organic solvent may contain a percentage of water. The water percentage may be about 1-30%, greater than about 10%, about 15-20% or the like.

In additional examples, the rear surface of the device includes a printed grid. The printed grid is visible on a front surface for colony counting after the liquid sample has absorbed and diffused throughout the absorbent matrix. Further, the device may be a waterproof plate and comprises a solid bottom and a thin peelable adhesive top.

The medium may further comprise a growth indicator color-developing agent. In some examples, the color-developing agent includes at least one of the following: triphenyltetrazolium chloride, 3-(p-iodophenyl)-2-(p-nitrophenyl)-5-phenyl-2H-tetrazolium chloride, 3-(4,5-dimethyl-2-thiazolyl)-2,5-diphenyl-2H-tetrazolium bromide, 5-bromo-3-indolyl-beta.-D-galactoside, bromothymol blue, and neutral red. The color-developing agent may include triphenyltetrazolium chloride. X=gal In some examples, the organic solvent comprises a C1-C5 alcohol. In yet other examples, the organic solvent comprises 2-propanol. The medium mixture may include a selective agent. The selective agent may comprise SDS. For instance, the selective agent may comprise bile salts, deoxycholate, sodium citrate or other gram negative selective agents.

Additional medium mixture examples include an enhancer. The enhancer may comprise isopropyl-β-D-thiogalactoside (IPTG) or another similar analogue to lactose. A color enhancer may comprise x-gal.

In particular examples, the fibrous material comprises Rayon, a Rayon derivative, the like or a combination thereof. The fibrous material may include cellulose acetate. Further, the fibrous material may comprise trilobal Rayon. In certain examples, the fibrous material comprises Rayon and wherein the Rayon has a weight of denier filament in the range of about 0.2 mm to about 1.0 mm. For instance the fibrous material comprises Rayon and wherein the Rayon has a denier per filament of about 0.8 to about 3.0.

The selective bacterial nutritive ingredient may comprise components of EC media. The adhesive may comprise polyvinyl pyrrolidone. In other examples the adhesive comprises polyethylene oxide.

In certain examples, the liquid sample is a liquid extract of solid, a partial solid, and a combination thereof.

Another aspect of the present disclosure is to provide a colloidal slurry matrix free of a mesh or weave. For instance, in a culture media device for detecting a microorganism, when present, in a liquid sample, a colloidal slurry matrix free of a mesh or weave may include an adhesive; a gelling agent; a bacterial nutritive ingredient; a plurality of Rayon fiber particles; a percent liquid organic solvent; and cellulosic material. Typically, the matrix is a liquid absorbent matrix having a uniform distribution of bacterial growth media that is generally adapted to absorb and evenly diffuse the liquid sample throughout the matrix.

Yet another aspect of the present disclosure is to provide a culture medium and method for detecting microorganisms in a sample, such as a milk sample, a water sample or other food sample, comprising a mixture that can include an adhesive, a gelling agent, a bacterial nutritive ingredient, a fibrous material, a percent liquid organic solvent, and cellulosic material. Upon addition to a waterproof and flat device and being allowed to dry or evaporate the liquid, the mixture forms a bacterial growth media-infused, liquid absorbent and diffusing, matrix that is adhered to the base of the waterproof and flat device.

The gelling agent can be, for example, one or more of tica gum, xanthan gum, locust bean gum, guar gum, carrageenan, or alginate. The adhesive, when present, can be, for example, one or more of Klucel (hydroxypropylcellulose), a solvent soluble cellulosic, for instance carboxymethylcellulose, polyvinyl pyrrolidone and polyethylene oxide. The culture medium bacterial nutritive ingredient can be, for example, EC media or one or more of its individual components thereof or other media and media components known in the art. In other examples, the bacterial nutritive ingredient can be plate count agar or its individual components. The culture medium can also include one or more growth indicator color-developing agents such as triphenyltetrazolium chloride, 3-(p-iodophenyl)-2-(p-nitrophenyl)-5-phenyl-2H-tetrazolium chloride, 3-(4,5-dimethyl-2-thiazolyl)-2,5-diphenyl-2H-tetrazolium bromide, 5-Bromo-4-Chloro-3-Indolyl-B-D-glucuronide; 6-Chloro-3-Indolyl-B-D-galactopyranoside; 5-bromo-3-indolyl-.beta.-D-galactoside, bromothymol blue, and neutral red. The organic solvent can include one or more of ethanol and isopropyl alcohol and can also include, in some aspects, a percentage of water, for example 1-30% water, more than 10% water or in the range of 15-20% water.

In other examples, the solvent can also include one or more alcohols, for example more than 50% or in the range of about 60% to about 80%. Useful alcohols include C1-C5 alcohols such as 2-propanol and ethanol. The waterproof flat plate can be made of, for example, plastic or glass and can be in a typical Petri dish configuration or in a clamshell-like configuration as shown in FIG. 1, and may also include PET plastics, polypropylene, polypropylene and the like. The culture medium can also include an enhancer such as IPTG or another similar analogue to lactose. The fibrous material can include materials such as Rayon or Rayon derivatives or similar materials such as trilobal Rayon, which can be used with a hydrophilic cellulose ester, such as cellulose acetate. The culture medium can also include one or more selective agents such as SDS, antibiotics, deoxycholate, citrate and/or bile salts.

Still another aspect of the present disclosure is to provide a culture device comprising a rear surface having a printed grid and a front surface. Typically, the printed grid is visible on the front surface for colony counting after a test has been developed. The culture medium may be a mixture of an adhesive, a gelling agent, a bacterial nutritive ingredient, a fibrous material, a percent liquid organic solvent and cellulosic material. In particular examples, the grid includes printed lines chosen from vertical, horizontal and a combination thereof.

In other examples, wherein upon addition to a waterproof and flat device and being allowed to dry or evaporate the liquid, the mixture forms a liquid absorbent matrix that includes a uniform distribution of bacterial growth media and is configured to absorb a liquid sample and allow said liquid sample to diffuse evenly in the matrix. For instance, when the liquid sample is added to any of the absorbent matrices shown and described herein, the sample disperses homogenously throughout the matrix. In any of the examples and embodiments herein, the liquid sample may be a liquid extract of a solid, partial solid, or the like. A waterproof flat plate may comprise plastic or glass. The waterproof and flat device may comprise a clamshell configuration. Further, the waterproof device may be polyvinylchloride or polystyrene.

In yet other examples, a culture medium device includes an adhesive; a gelling agent; a bacterial nutritive ingredient; a fibrous material; a waterproof flat plate having a rear surface with a printed grid and a front surface whereby the printed grid is visible on the front surface, a percent liquid organic solvent; and a cellulosic material. Typically, wherein upon addition to a waterproof and flat device and being allowed to dry or evaporate the liquid, the mixture forms a liquid absorbent matrix that includes a uniform distribution of bacterial growth media and is configured to absorb a liquid sample and allow said liquid sample to diffuse evenly throughout.

Yet another aspect of the disclosure is to provide a method for detection of microorganisms, when present, in a liquid sample. The method may include mixing any of materials shown and described herein to create a slurry; dispensing the slurry onto a waterproof and flat device; evaporating the slurry to form a matrix; dispensing the liquid sample onto the matrix; and absorbing the liquid sample into the matrix. Typically, the ingredients to create the slurry include an adhesive, a gelling agent, a bacterial nutritive ingredient, a fibrous material, a percent liquid organic solvent. The method may further include observing growth of the microorganism, when present, on the matrix.

The above summary was intended to summarize certain embodiments of the present disclosure. Embodiments will be set forth in more detail in the figures and description of embodiments below. It will be apparent, however, that the description of embodiments is not intended to limit the present inventions, the scope of which should be properly determined by the appended claims.

BRIEF DESCRIPTION OF THE DRAWINGS

Embodiments of the disclosure will be better understood by a reading of the Description of Embodiments along with a review of the drawings, in which.

DESCRIPTION OF EMBODIMENTS

Figure 1:
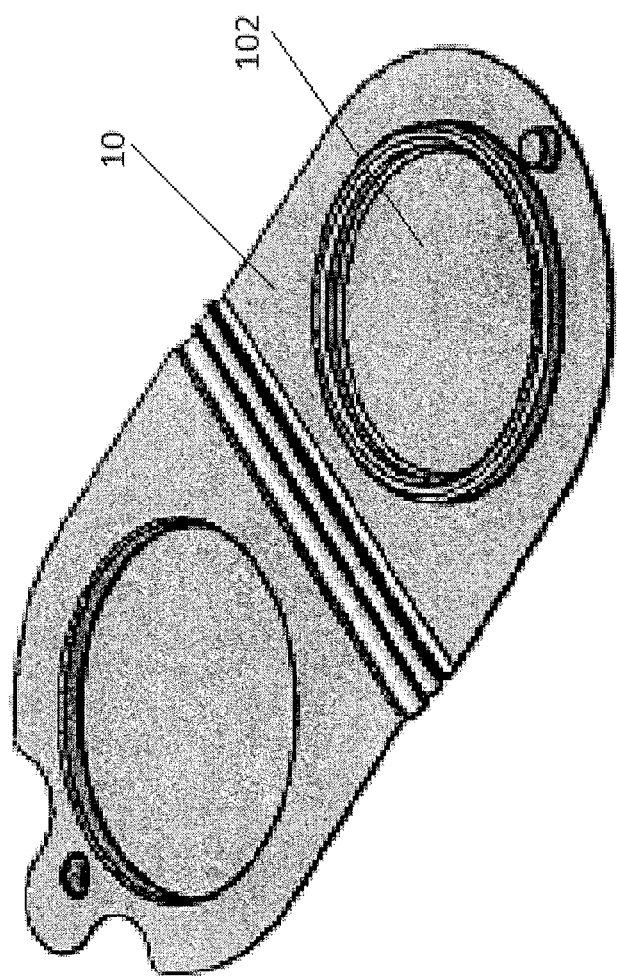
FIG. 1 is a top perspective view of one embodiment of a device having a flat surface, in a clamshell format.

In the following description, like reference characters designate like or corresponding parts throughout the several views. Also in the following description, it is to be understood that such terms as "forward," "rearward," "left," "right," "upwardly," "downwardly," and the like are words of convenience and are not to be construed as limiting terms.

The media can include any or all of a partially water-soluble gelling agent, nutritive ingredients, one or more selective inhibitors, one or more indicators, one or more enhances, one or more adhesive, alcohol, water and a fiber-like material. In particular examples, the fiber materials are small cut Rayon particles, for instance Rayon particles. The Rayon particles may be a variety of sizes and dimensions as described herein, including, but not limited to, about 0.1 millimeters to about 10 millimeters, including about 0.2 millimeters to about 3.0 millimeters. The media ingredients are combined and mixed to form a colloidal slurry. The slurry is dispensed into a culture device such as, or similar to, a conventional Petri dish or a clamshell-like device such as shown in FIG. 1. After dispensing the slurry is dried. Drying the slurry forms a papercloth-like matrix that is relatively evenly distributed within the culture device. In particular examples, the papercloth-like matrix has no mesh or weave.

The matrix, having been formed from the slurry, is infused with the slurry components including the components required for selectively or non-selectively culturing and detecting microorganisms. The papercloth-like characteristics, including wicking of test sample/liquid, allows for easy sample application directly thereon. Wicking characteristics of the matrix assists in the uniform distribution of the sample across the surface area of the matrix, for instance on pipetting, without the need for a spreading device or an operator manipulation. In particular examples, the uniform distribution characteristics of the matrix minimize, or eliminate, sample pooling and/or ensure proper sample traversing across any of the matrix examples shown and described herein.

On sample addition the matrix forms a pseudo-solid gel. Such a gel can be created either using heat or, alternatively and preferably, without the need for heat. The gel allows the sample to be inverted and incubated. Any of the examples and embodiments shown and described herein may be incubated several times at a variety of temperatures and at a variety of incubation lengths. For instance, multiple incubations may include 25, 32, 37, 55, 60 degree centigrade incubations, and the like incubations. If microbes, such as bacteria, are present in the sample, their motility and diffusion are restricted causing formation of distinct growth colonies equivalent to the number of, for example, aerobic bacteria in the sample.

Any of the examples and embodiments herein may test a variety of aerobic bacteria, including, but not limited to, gram negative bacteria such as *Salmonella,* Enterobacteriaceae, *Escherichia coli,* including *e. coli* 0157, and *Vibrio parahaemolyticus* gram positive bacteria including *Listeria monocytogenes* and *Staphylococcus aureus.* Other possible application include tests for yeast, mold and tests to detect broad categories and mixtures of microbes, such as heterotrophic bacteria, lactic acid bacteria and total plate counts.

Inoculation of a bacterial fluid into the simple culture medium is usually carried out through a method in which a certain amount of the fluid is inoculated into the medium on any of the culture devices described herein by use of, for example, a pipette.

The culture device can be a waterproof flat plate onto which the aforementioned fibrous water-absorbent sheet adheres may be formed from any waterproof material such as plastic or glass, but is preferably formed from transparent material so as to enable observation from the outside, including any of the printed grids shown and described herein. The culture device can include a cover or be in a clamshell-like configuration (e.g. FIG. 1). The device can be made of polystyrene, glass, plastic, or similar material. In a clamshell configuration the device can be made from PVC or other flexible plastic material such as PET, or polyethylene. Regardless of the device configuration, upon drying of the slurry an in-situ created, media-infused paperclothlike matrix can be formed. An ingredient of the slurry can be a water-soluble gelling agent. The gelling agent can be chosen for the characteristic that it will not set-up in organic solvents such as the ethanol, or other organic solvent in which the slurry is created.

A wide variety of gelling agents can be employed to provide for the formation of the matrix. The gelling agent can be generally transparent with a gel-like consistency. The gelling agent should not substantially or functionally affect the growth of the bacteria during incubation or have any adverse affect on any of the ingredients or the test results. The gelling agent should be transparent or relatively colorless, so as not to interfere with the quantitative counting of the microorganism detected. Xantham gum is one example of a useful gelling agent. Other suitable gelling agents include both natural and synthetic gelling agents. such as locust bean, guar gum and thickening or gluing agents such as hydroxyethyl cellulose, carboxymethyl cellulose, polyacrylamide, carrageenan, and alginate, as well as superabsorbent materials, including glycol modified polysaccharides, such as Ucargel, super absorbent agents (Union Carbide, Boundbrook, N.J.), and starch-graft-poly(sodium acrylate-co-acrylamides), such as WATER LOCK™ super absorbent agents (Grain processing Corp., Muscatine, Iowa), are suitable gelling agents.

The media can be included with an organic liquid solvent such as C1-C5 alcohols such as ethanol, 2-propanol and isopropyl alcohol.

Natural and/or manmade wicking fibers such as cellulosic and/or cellulosic-like material such as cotton and/or Rayon and Rayon derivatives and similar materials such as trilobal Rayon, can be included along with a material such as cellulose acetate or other hydrophilic cellulose esthers to create, in-situ, the papercloth-like material. Useful Rayon particle size range about 0.2 mm to about 1.0 mm with a denier per filament (dpf) in the range of about 0.8 dpf to about 3 dpf and higher. Useful trilobal Rayon size and weight in denier per filament (dpf) are similar to Rayon and can tend to useful at higher size and dpf ranges.

Water can also be included to partially swell the gel and to enhance the spreading, gluing and even distribution of the slurry. Water can also be used to make the slurry produced matrix more susceptible to even sample distribution. For example, without water, or with reduced water content, sample application such as by pipetting, can cause the matrix to flow with the sample addition and move away from the sample application area in a kind of ripple affect. That is, addition of the sample can cause an undesirable clearing of the matrix away from the sample application area. This occurs due to lack of gel-like consistency of the matrix before sample application. The ingredients tend to spread away from the point of sample application if not partially congealed by the partially swelled gum. The presence of water can prevent such unwanted matrix movement and by partially swelling the gum which would not occur if the solvent were only ethanol or another alcohol.

An adhesive agent can be included to adhere the paper-like matrix to the device. By including a material such as Klucel (hydroxypropylcellulose) a glue-like affect can be created where the material bonds the paper-like matrix to the bottom of the device which typically will be in the form of a plate or other solid support. The Klucel (hydroxypropylcellulose) completely or partially dissolves in the solvent and, when dried, becomes glue to adhere the matrix to the device. Adherence of the matrix to the device allows for ease of handling and prevents the matrix from separating from the base of the device. Useful adhesives will be at least partially soluble in water and alcohol. Examples of the adhesive include hydroxypropyl cellulose, polyvinyl pyrrolidone, and polyethylene oxide. In some embodiments, the media-infused matrix can be configured to adhere to the culture device without use of an adhesive.

The method and devices described herein provide a culture medium in which a test fluid inoculated thereto diffuses rapidly and relatively uniformly through the media-infused matrix that is adhered to the device such as a plate. The adherence to the plate allows sample addition and incubation in an inclined position or on an uneven or flat surface state, an inverted state, or a gravity-free state, as well as in an even state; enabling detection and identification of microorganisms through a simple operation; and facilitating transportation, sterilization, etc. of the medium.

By including a material such as rayon and/or trilobal rayon within the media in combination with a material such as cellulose acetate, a liquid-absorbent matrix can be created in-situ that is infused with media. The in-situ creation of the matrix, sufficiently and uniformly infused with the media, eliminates the requirement for use of, for example, a patterned sheet, such as the dry sheet of nonwoven cloth used in the commercially available test known as COMPACT DRY (from Nissui Pharmaceutical, Japan) thereby further simplifying testing and reducing production cost. The presence of material such as xanthan gum also can assist in maintaining the uniformity of the media.

A variety of media, that will support the growth of aerobic bacteria including coliforms are usefully employed. For total aerobic counts a relatively rich media is useful. Such rich media can include media components such as peptone, yeast extract and dextrose as well as a detection substrate that changes color such as triphenyltetrazolium chloride (TTC). For more selective detection, such as detection of coliforms, selective media can be usefully employed.

Examples of suitable nutrients include amino acids, such as from meat peptone, casein peptone, beef extract, carbohydrates, such as dextrose, lactose, glucose, galactose, as well as fats, minerals and vitamins, such as from yeast extract. Examples of suitable nutrient formulations include Violet Red Bile, Standard Methods, and Baird-Parker nutrient formulations (Acumedia, Inc., Baltimore, Md.) and EC Media (See e.g., Example 2).

Selective agents such as hydrophilic selective agents that can be incorporated into the slurry to provide a means for selectively inhibiting or identifying microorganisms can include antibiotics, such as colistin methane sulfonate or nalidixic acid, and non-ionic and ionic detergents such as sodium dodecyl sulfate, SDS. Other suitable inhibitory selective agents can include inhibitory salts, such as bile salts that, for example, can be used to selectively grow gram-negative microorganisms (i.e., inhibit the growth of gram-positive microorganisms).

Other useful indicator agents can include dyes that are metabolized by, or otherwise react with, growing microorganisms to cause the microbial colonies to be colored or fluoresce for ease of visualization and quantification. Examples of such dyes include triphenyl tetrazolium chloride, p-tolyl tetrazolium red, tetrazolium violet, veratryl tetrazolium blue, crystal violet, neutral red, and 5-bromo-4-chloro-3-indolyl phosphate disodium salt. Particularly preferred dyes in accordance with the present invention include crystal violet, neutral red and 5-bromo-4-chloro-3-indolyl phosphate disodium salt. Other suitable dyes can be used depending on the particular organism(s) to be identified. Examples of colorimetric reagents which can be employed as substrates for β-galactosidase, such as for coliform detection, include O-nitrophenyl-β-D-thiogalactoside (ONPG), 5-bromo-4-chloro-3-indolyl-β-D-galactoside (X-GAL), and chlorophenol red β, D-galactopyranoside (CPRG). Other possible indicators include glucuronidase, α-galactosidase, chlorophenol red B-D-galactopyranoside, glucosidase, escalinase, pH and optical density.

A goal in selecting media for coliform detection is to enhance target enzyme production, such as β-galactosidase production, and to limit the available carbohydrate, other than the color or fluorescent indicator(s), upon which β-galactosidase can act. To enhance β-galactosidase the media can include synthetic inducers. Two known synthetic inducers of β-galactosidase are isopropyl-β-D-thiogalactoside (IPTG) and methyl-β-D-thiogalactoside (TMG). One or more color or fluorogenic indicators may be included as part of the media.

Examples of the color-developing agent include dyes which color colonies, such as triphenyltetrazolium chloride, 3-(p-iodophenyl)-2-(p-nitrophenyl)-5-phenyl-2H-tetrazolium chloride, and 3-(4,5-dimethyl-2-thiazolyl)-2,5-diphenyl-2H-tetrazolium bromide; enzyme substrates such as 5-bromo-3-indolyl-.beta.-D-galactoside; 5-Bromo-4-Chloro-3-Indolyl-B-D-glucuronide; 6-Chloro-3-Indolyl-B-D-galactopyranoside; and pH indicators such as Bromothymol Blue and Neutral Red and oxidation/reduction indicators.

It may also be possible to combine indicators, such as combining color indicators with fluorogenic indicators. By combining indicators, for example with an indicator that is visible to the eye under ambient light, and an indicator that requires some instrumentation but may be more sensitive, the user can be provided more flexibility. This is particularly feasible when inducing enzyme production, such as galactosidase with IPTG, and using MUG-GAL as a fluorescent indicator of cell lysis. It may be further beneficial to combine the colorimetric indicator X-GAL with the fluorogenic indicator MUG-GAL.

When detection of microorganisms is carried out by use of the simple culture medium of the present invention, a test fluid is inoculated into the surface of the medium. After inoculation, the test fluid diffuses readily in the medium, followed by occurrence of swelling and gelation; microorganisms contained in the test fluid are trapped in the resultant gel; free movement of the microorganisms is suppressed; and colonies are formed through culture. Therefore after temperature incubation for a period of time and through observation of the surface of the medium, formation of microbial colonies can be easily observed. When a sample is quantitatively inoculated into the simple culture medium, the number of bacteria contained in the sample can be easily calculated by counting colonies formed after culture of the sample.

Figure 2:
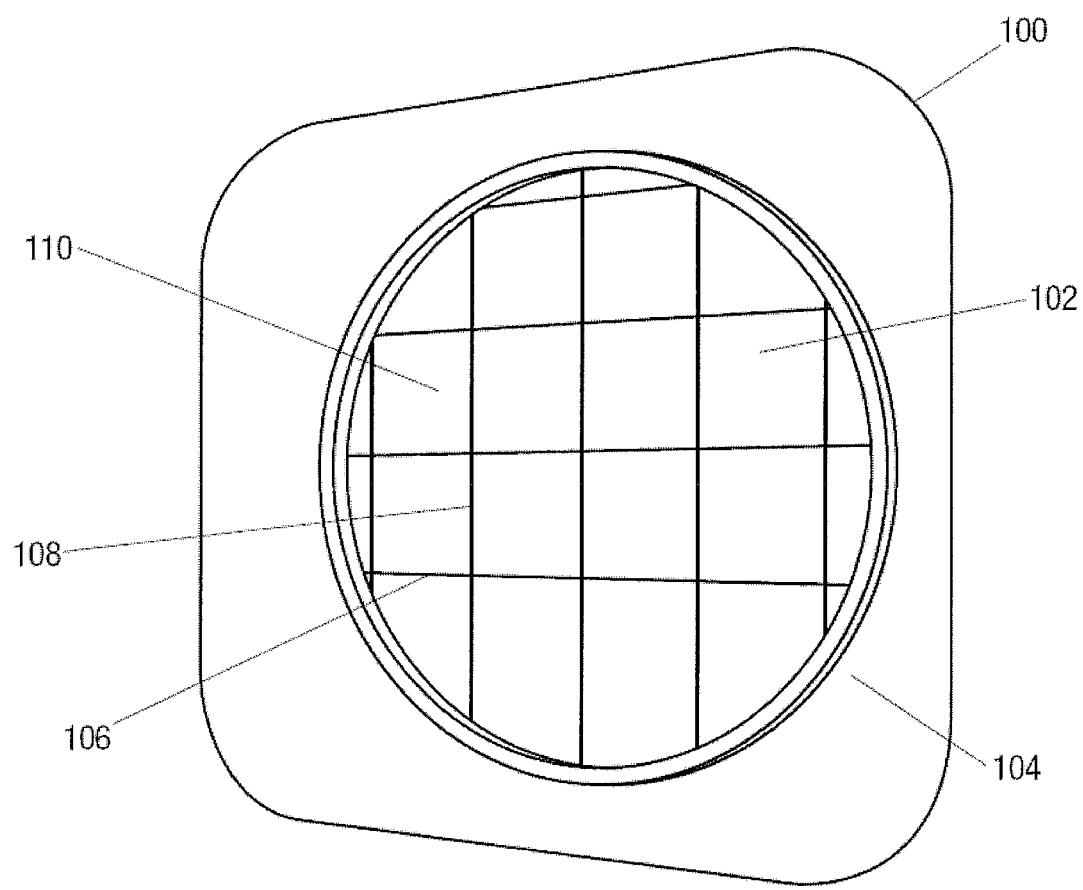
FIG. 2 is a top perspective view of one embodiment of an improved culture device embodiment according to the disclosure.

FIG. 2 introduces yet another embodiment of elements described herein. As shown in FIG. 2, the culture device 100, and/or plate media devices or similar packaging described herein, may include a grid 110. The grid 110 may have a horizontal 108 and/or vertical 106 component useful for colony counting. In particular examples, the grid 110 is printed on the rear surface 104. The grid 110 may be printed in a variety of ways, including inkjet printing, pad printing and the like. Regardless of the printing type, the grid 110 is visible through the generally transparent culture device to the front surface 102. In particular examples, the grid 110 is visible front the front surface 102 for colony counting after any of the tests described herein have been developed.

The following experiments demonstrate the efficacy and utility of the present inventions.

EXAMPLES

On dispensing the colloidal slurry into the plastic mold/device and drying, a paper-like matrix is created that is infused with media and is capable of wicking a liquid sample for relatively even sample distribution throughout. On adding a volume of a water-based-sample, such as food slurry or a food or environmental testing sample or urine or serum, the sample is wicked across the device through the matrix and the media components and the gelling agent sets to make a pseudo-solid gel that does not pour out or drop when flipped upside down and incubated. The device lid, which can be, for example in the form of a clamshell-like lid or Petri dish lid is placed over the gel to prevent evaporation during incubation that can take between 12 hours and 5 days. Depending on the growth, indicator and selective agents, and temperature and time of incubation, specific microorganism types can be detected and quantified.

Example 1

The following formulation was used to detecting total bacteria in milk. The results in Table 1 reflect a comparison to conventional nutrient broth agar Petri dish determination following Standard Method of Dairy Analysis. The formulation used to create the slurry was as follows:

| Material | % Weight/Volume |
| --- | --- |
| Water | 17.667% |
| Ethanol 100% (200 proof) | 70.668% |
| Klucel-hydroxypropylcellulose | 0.442% |
| Cellulose Acetate | 2.650% |
| Xanthan Gum | 2.650% |
| Glucose | 0.177% |
| Tryptone | 0.883% |
| Yeast Extract | 0.442% |
| Triphenyltetrazolium Chloride (TTC) | 0.004% |
| Rayon 0.8 dpf 0.2 mm | 4.417% |

The slurry was added to a standard plate and allowed to dry in a 37 degree C. incubator overnight. The results displayed in Table 1 compare the Total Plate Formulation (as specified above) with the Standard Method at various sequential dilutions of bacteria for different milk samples.

TABLE 1

Total Plate Formulation Compared to Standard Method

| Sample | Total Count Formulation Colony Forming Units/mL | | Standard Methods Method Colony Forming Units/mL | |
| --- | --- | --- | --- | --- |
| Milk 1-10-2 Dilution | 2 | 27 | 45 | 36 |
| Milk 1-10-3 Dilution | 2 | 2 | 2 | 1 |
| Milk 2-10-2 Dilution | 30 | 34 | 87 | 83 |
| Milk 2-10-3 Dilution | 9 | 9 | 7 | 8 |
| Milk 3-10-2 Dilution | 7 | 5 | 11 | 24 |
| Milk 4-10-3 Dilution | 6 | 4 | 5 | 8 |
| Milk 5-10-2 Dilution | 47 | 50 | 70 | 72 |
| Milk 5-10-3 Dilution | 5 | 5 | 4 | 14 |
| Milk 6-10-3 Dilution | 6 | 6 | 8 | 7 |
| Milk 7-10-2 Dilution | 8 | 3 | 4 | 2 |
| Milk 8-10-2 Dilution | 30 | 22 | 57 | 55 |
| Milk 8-10-3 Dilution | 3 | 2 | 4 | 8 |

Example 2

The following formulation was used to detecting coliform bacteria in milk. The results in Tables 2 reflect a comparison to conventional coliform selective agar Petri dish determination (VBRB agar Petri dish determination) following Standard Method of Dairy Analysis.

The formulation used to create the slurry was as follows:

| Material | % Weight Volume |
| --- | --- |
| Water | 17.354% |
| Ethanol 100% (200 proof) | 69.417% |
| Klucel-hydroxypropylcellulose | 0.434% |
| Cellulose Acetate | 2.603% |
| Xanthan Gum | 2.603% |
| SDS | 0.004% |
| EC Media | 3.211% |
| IPTG | 0.021% |
| X-GAL | 0.014% |
| Rayon 0.8 dpf 0.2 mm | 4.339% |

The slurry was added to a standard plate and allowed to dry. The results displayed in Table 2 are from experiments comparing the Coliform Formulation (as specified in Example 2 above) with the Standard Method at various sequential dilutions of bacteria for two different milk samples.

TABLE 2

Coliform Plate Formulation Compared to Standard Method

| Sample | Total Count Formulation Colony Forming Units/mL | | Standard Methods VBRB Method Colony Forming Units/mL | |
| --- | --- | --- | --- | --- |
| Milk 1-undiluted | 33 | 37 | 56 | 61 |
| Milk 1-10-1 Dilution | 4 | 1 | 5 | 1 |
| Milk 2- | 159 | 146 | 239 | 278 |

TABLE 2-continued

Coliform Plate Formulation Compared to Standard Method

| Sample | Total Count Formulation Colony Forming Units/mL | | Standard Methods VBRB Method Colony Forming Units/mL | |
|---|---|---|---|---|
| undiluted Milk 2-10-1 Dilution | 36 | 45 | 31 | 45 |
| Milk 3-10-1 Dilution | 15 | 11 | 7 | 8 |
| Milk 4-undiluted | 136 | 139 | 143 | 154 |
| Milk 4-10-1 Dilution | 13 | 15 | 3 | 0 |
| Milk 5-undiluted | 49 | 54 | 77 | 80 |
| Milk 5-10-1 Dilution | 3 | 1 | 0 | 2 |
| Milk 6-undiluted | 85 | 71 | 79 | 79 |
| Milk 6-10-1 Dilution | 4 | 1 | 4 | 2 |
| Milk 7-undiluted | 35 | 39 | 41 | 43 |
| Milk 7-10-1 Dilution | 2 | 5 | 3 | 1 |

Numerous characteristics and advantages have been set forth in the foregoing description, together with details of structure and function. Many of the novel features are pointed out in the appended claims. The disclosure, however, is illustrative only, and changes may be made in detail, especially in matters of shape, size, and arrangement of parts, within the principle of the disclosure, to the full extent indicated by the broad general meaning of the terms in which the general claims are expressed. It is further noted that, as used in this application, the singular forms "a," "an," and "the" include plural referents unless expressly and unequivocally limited to one referent.

We claim:

1. A culture medium mixture to be applied to a device having a flat surface to define an adhered colloidal complex, said culture medium mixture comprising:
   a. an adhesive;
   b. an gelling agent;
   c. a bacterial nutritive ingredient;
   d. a fibrous material;
   e. a liquid organic solvent; and
   f. a cellulosic, fibrous material mixture, and wherein said adhesive substantially dissolves in said solvent and wherein upon drying or evaporation of the mixture adheres said fibrous material on the device, the mixture forms said adhered colloidal complex on said flat surface being matrix free of a mesh or weave, and adapted to allow absorbing and evenly diffusing a water-based liquid sample throughout the sample absorbent matrix.

2. The culture medium mixture of claim 1, wherein the gelling agent is selected from the group consisting of xanthan gum, tica gum, locust bean gum, guar gum, carrageenan, and alginate.

3. The culture medium mixture of claim 1 wherein the adhesive agent is selected from the group consisting of hydroxypropylcellulose, hydroxylmethl cellulose, and solvent soluble cellulosics.

4. The culture medium mixture of claim 1 further comprising a growth indicator color-developing agent.

5. The culture medium mixture of claim 1 wherein the organic solvent comprises ethanol or isopropyl alcohol.

6. The culture medium of claim 1 wherein the water percentage is chosen from about 1-30%, greater than about 10%, and about 15-20%.

7. The culture medium mixture of claim 1 wherein a rear surface of said device includes a printed grid.

8. The culture medium mixture of claim 7 wherein the printed grid is visible on a front surface for colony counting after said liquid sample has absorbed and diffused throughout the absorbent matrix.

9. The culture medium mixture of claim 5 wherein the alcohol percentage is more than about 50%.

10. The culture medium mixture of claim 4, wherein the color-developing agent is selected from the group consisting of triphenyltetrazolium chloride, 3-(p-iodophenly)-2-(p-nitrophenyl)-5-phenyl-2H-tetrazolium chloride, 3-(4.5-dimethyl-2-thiazolyl)-2.5-diphenyl-2H-tetrazolium bromide, 5-bromo-3-indolyl-beta. -D-galactoside, bromothymol blue, and natural red.

11. The culture medium mixture of claim 1, wherein the device is a waterproof plate and comprises a solid bottom and a thin peelable adhesive top.

12. The culture medium mixture of claim 1 further comprising an enhancer.

13. The culture medium mixture of claim 12 wherein the enhancer comprises isopropyl-$\beta$-D-thiogalactoside or another similar analogue to lactose.

14. The culture medium mixture of claim 1 further comprising a selective agent.

15. The culture medium mixture of claim 14 wherein the selective agent comprises SDS.

16. The culture medium mixture of claim 1 wherein the liquid sample is an extract chosen from a solid, a partial solid, and a combination thereof.

17. A culture medium assembly comprising
   a. a mixture comprising:
      i. an adhesive,
      ii. an gelling agent,
      iii. a bacterial nutritive ingredient,
      iv. a fibrous material,
      v. a liquid organic solvent, and
      vi. a cellulosic, fibrous material mixture; and
   b. a substantially flat surface device to receive said mixture as an adhered colloidal complex, wherein said adhesive substantially dissolves in said solvent and wherein upon drying or evaporation of the mixture adheres said fibrous material on the device, and
   wherein said mixture forms an adhered colloidal complex matrix free of a mesh or weave, and adapted to allow absorbing and evenly diffusing a water-based liquid sample throughout the adhered colloidal complex.

* * * * *